United States Patent [19]

Gericke et al.

[11] Patent Number: 5,112,972
[45] Date of Patent: May 12, 1992

[54] SYNTHESIS OF CHROMAN DERIVATIVES

[75] Inventors: Rolf Gericke, Seeheim; Manfred Baumgarth; Ingeborg Lues, both of Darmstadt; Rolf Bergmann, Reichelsheim, all of Fed. Rep. of Germany; De Peyer, Bern, Switzerland

[73] Assignee: Merck Patent Gesellschaft Mit Beschrankter Haftung, Darmstadt, Fed. Rep. of Germany

[21] Appl. No.: 531,490

[22] Filed: May 31, 1990

[30] Foreign Application Priority Data

Jun. 2, 1989 [DE] Fed. Rep. of Germany ....... 3918041

[51] Int. Cl.$^5$ .......................................... C07D 237/00
[52] U.S. Cl. .................................. 544/230; 544/238
[58] Field of Search ............... 544/230, 238; 514/253; 536/4.1, 18.1

[56] References Cited

U.S. PATENT DOCUMENTS

| | | | |
|---|---|---|---|
| 4,446,113 | 5/1984 | Evans et al. | 422/267 |
| 4,542,149 | 9/1985 | Evans et al. | 514/422 |
| 4,640,928 | 2/1987 | Willcocks | 512/422 |
| 4,644,070 | 2/1987 | Evans et al. | 549/399 |
| 4,772,603 | 9/1988 | Evans | 514/241 |
| 4,786,639 | 11/1988 | Evans | 514/254 |

FOREIGN PATENT DOCUMENTS 3726261 6/1989 Fed. Rep. of Germany .

OTHER PUBLICATIONS

Morrison & Boyd, Organic Chemistry, 3rd Ed., Allyn & Bacon, Inc., publ., p. 555.

Primary Examiner—C. Warren Ivy
Assistant Examiner—Catherine Scalzo
Attorney, Agent, or Firm—Millen, White & Zelano

[57] ABSTRACT

The invention relates to new chroman derivatives of the formula I

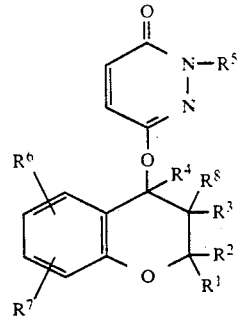

in which
$R^1$ is A,
$R^2$ and $R^8$ are each H or A,
$R^1$ and $R^2$ together are also alkylene with 3–6 C atoms,
$R^3$ is OH, OA or OAc,
$R^4$ is H,
$R^3$ and $R^4$ together are also a bond,
$R^5$ is Ar or $C_nH_{2n}$-$R^9$,
$R^9$ is alkenyl or alkynyl with 2–4 C atoms in each case, OH, OA, CHO, CO-A, CS-A, COOH, COOA, COO-alkyl-Ar, CS-OA, $NO_2$, $NH_2$, NHA, $NA_2$, CN, F, Cl, Br, I, $CF_3$, SA, SO-A, $SO_2$-A or Ar,
Ar is a phenyl group which is unsubstituted or substituted once or twice by $R^{10}$, $R^6$, $R^7$ and $R^{10}$ are each H, A, HO, AO, CHO, ACO, $CF_3CO$, ACS, HOOC, AOOC, AO-CS, ACOO, A-CS-O, hydroxy-alkyl, mercapto-alkyl, $NO_2$, $NH_2$, NHA, $NA_2$, CN, F, Cl, Br, I, $CF_3$, AS, ASO, $ASO_2$, AO-SO, $AO-SO_2$, AcNH, AO-CO-NH, $H_2NSO$, HANSO, $A_2NSO$, $H_2NSO_2$, $HANSO_2$, $A_2NSO_2$, $H_2NCO$, HANCO, $A_2NCO$, $H_2NCS$, HANCS, $A_2NCS$, ASONH, $ASO_2NH$, AOSONH, $AOSO_2NH$, ACO-alkyl, nitro-alkyl, cyano-alkyl, A-C(=NOH), A-C(=NNH$_2$), $H_2PO_3$ or $A_2PO_3$,
n is 1, 2 or 3,
A is alkyl with 1–6 C atoms,
-alkyl is alkylene with 1–6 C atoms and
AC is alkanoyl with 1–8 C atoms or aroyl with 7–11 C atoms, and the salts thereof which display effects on the cardiovascular system and can be used for the treatment or prophylaxis of heart failure, angina pectoris, high blood pressure, incontinence and alopecia.

3 Claims, No Drawings

SYNTHESIS OF CHROMAN DERIVATIVES

SUMMARY OF THE INVENTION

The invention relates to new chroman derivatives of the formula I

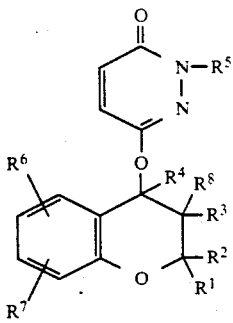

in which
$R^1$ is A,
$R^2$ and $R^8$ are each H or A,
$R^1$ and $R^2$ together are also alkylene with 3-6 C atoms,
$R^3$ is OH, OA or OAc,
$R^4$ is H,
$R^3$ and $R^4$ together are also a bond,
$R^5$ is Ar or $C_nH_{2n}$-$R^9$,
$R^9$ is alkenyl or alkynyl with 2-4 C atoms in each case, OH, OA, CHO, CO-A, CS-A, COOH, COOA, COO-alkyl-Ar, CS-OA, $NO_2$, $NH_2$, NHA, $NA_2$, CN, F, Cl, Br, I, $CF_3$, SA, SO-A, $SO_2$-A or Ar,
Ar is a phenyl group which is unsubstituted or substituted once or twice by $R^{10}$,
$R^6$, $R^7$ and $R^{10}$ are each H, A, HO, AO, CHO, ACO, $CF_3CO$, ACS, HOOC, AOOC, AO-CS, ACOO, A-CS-O, hydroxyalkyl, mercapto-alkyl, $NO_2$, $NH_2$, NHA, $NA_2$, CN, F, Cl, Br, I, $CF_3$, AS, ASO, $ASO_2$, AO-SO, $AO-SO_2$, AcNH, AO-CO-NH, $H_2NSO$, HANSO, $A_2NSO$, $H_2NSO_2$, $HANSO_2$, $A_2NSO_2$, $H_2NCO$, HANCO, $A_2NCO$, $H_2NCS$, HANCS, $A_2NCS$, ASONH, $ASO_2NH$, AOSONH, $AO$-$SO_2NH$, ACO-alkyl, nitro-alkyl, cyano-alkyl, A-C(=NOH), A-C(=$NNH_2$), $H_2PO_3$ or $A_2PO_3$,
n is 1, 2 or 3,
A is alkyl with 1-6 C atoms,
-alkyl is alkylene with 1-6 C atoms and
Ac is alkanoyl with 1-8 C atoms or aroyl with 7-11 C atoms,
and the salts thereof.

The invention had the object of finding new compounds with valuable properties, in particular those which can be used for the preparation of medicaments.

It has been found that the compounds of the formula I and the physiologically acceptable salts thereof have valuable pharmacological properties while being well tolerated. Thus, they display effects on the cardiovascular system, it being possible to observe as a rule a selective attack on the coronary system at lower doses and a reducing effect on blood pressure at higher doses. For example, a decrease in resistance and an increase in flow occur in the coronary system, while the effect on the heart rate remains low. In addition, the compounds display a relaxant effect on various smooth-muscular organs (gastrointestinal tract, respiratory system and uterus). The effects of the compounds can be measured using methods known per se, such as are indicated, for example, in EP-A1-76075, EP-A1-173848 or AU-A-45547/85 (Derwent Farmdoc No. 86081769) and by K. S. Meesmann et al., Arzneimittelforschung 25 (11), 1975, 1770-1776. Examples of suitable experimental animals are mice, rats, guinea pigs, dogs, cats, monkeys or pigs.

The compounds can therefore be used as active compounds in medicaments in human and veterinary medicine They can also be used as intermediates for the preparation of other active compounds for medicaments.

A in the indicated formulae is a preferably unbranched alkyl group with 1-6, preferably 1-4, especially 1, 2 or 3, C atoms, specifically preferably methyl, also preferably ethyl, propyl, isopropyl, butyl, isobutyl, and furthermore preferably sec.-butyl, tert.-butyl, pentyl, isopentyl, (3-methylbutyl), hexyl or isohexyl (4-methylpentyl).

If $R^1$ and $R^2$ together are alkylene, the alkylene group is preferably unbranched, specifically preferably —$(CH_2)_x$—, where x is 3, 4, 5 or 6. The group "-alkyl" is preferably —$CH_2$— or —$CH_2CH_2$—.

Ac is preferably alkanoyl with 1-6, especially 1, 2, 3 or 4, C atoms, specifically preferably formyl or acetyl, also preferably propionyl, butyryl, isobutyryl, pentanoyl or hexanoyl, and furthermore preferably benzoyl, o-, m- or p-toluyl, 1- or 2-naphthoyl.

$R^1$ and $R^2$ are preferably each alkyl, especially each methyl or ethyl, preferably each methyl, and in addition $R^1$ and $R^2$ together are preferably —$(CH_2)_4$— or —$(CH_2)_5$—.

If $R^4$ is H, $R^3$ is preferably OH, also preferably O-CHO or O-$COCH_3$.

Ar is preferably unsubstituted phenyl. If Ar is a subtituted phenyl group, this is preferably substituted once.

The parameter n is preferably 1 or 2.

Alkenyl is preferably vinyl, as well as preferably 1-propenyl or allyl.

The preferred meanings in $R^6$, $R^7$ and $R^{10}$ are:
Methyl, also ethyl;
AO: Methoxy, also ethoxy;
ACO: Acetyl, also propionyl;
ACS: Thioacetyl, also thiopropionyl;
AOOC: Methoxycarbonyl, also ethoxycarbonyl;
AO-CS: Methoxy-thiocarbonyl, also ethoxythiocarbonyl;
ACOO: Acetoxy, also propionoxy;
ACSO: Thio(no)acetoxy, also thio(no)propionoxy;
Hydroxyalkyl: Hydroxymethyl or 1- or 2-hydroxyethyl;
Mercaptoalkyl: Mercaptomethyl or 1- or 2-mercaptoethyl;
NHA: Methylamino, also ethylamino;
$NA_2$: Dimethylamino, also diethylamino;
ASO: Methylsulfinyl, also ethylsulfinyl;
$ASO_2$: Methylsulfonyl, also ethylsulfonyl;
AO-SO: Methoxy-sulfinyl, also ethoxy-sulfinyl;
$AO-SO_2$: Methoxy-sulfonyl, also ethoxy-sulfonyl;
Ac-NH: Acetamido, also formamido, propionamido or benzamido;
AO-CO-NH Methoxycarbonylamino, also ethoxycarbonylamino;
HANSO: Methylaminosulfinyl, also ethylaminosulfinyl;
$A_2NSO$: Dimethylaminosulfinyl, also diethylaminosulfinyl;

HANSO$_2$: Methylaminosulfonyl, also ethylaminosulfonyl;

A$_2$NSO$_2$: Dimethylaminosulfonyl, also diethylaminosulfonyl;

HANCO: N-methylcarbamoyl, also N-ethylcarbamoyl;

A$_2$NOC: N,N-dimethylcarbamoyl, also N,N-diethylcarbamoyl;

HANCS: N-methyl-thiocarbamoyl, also N-ethyl-thiocarbamoyl;

A$_2$NCS: N,N-dimethyl-thiocarbamoyl, also N,N-diethyl-thiocarbamoyl;

ASONH: Methylsulfinylamino, also ethylsulfinylamino;

ASO$_2$NH: Methylsulfonylamino, also ethylsulfonylamino;

AOSONH: Methoxysulfinylamino, also ethoxysulfinylamino;

AOSO$_2$NH: Methoxysulfonylamino, also ethoxysulfonylamino;

ACO-alkyl: 2-oxopropyl, 2-oxobutyl, 3-oxobutyl, 3-oxopentyl-;

Nitroalkyl: Nitromethyl-, 1- or 2-nitroethyl;

Cyanoalkyl: Cyanomethyl, 1- or 2-cyanoethyl;

A-C(=NOH): 1-Oximinoethyl, also 1-oximinopropyl;

A-C(=NNH$_2$): 1-Hydrazonoethyl, also 1-hydrazonopropyl.

The radicals $R^6$ and $R^7$ are preferably located in the 6 and 7 position of the chroman system. However, they can also be in the 5 and 6, 5 and 7, 5 and 8, 6 and 8, and 7 and 8 position.

One of the radicals $R^6$ and $R^7$ is preferably H, while the other is different from H. This other radical is preferably located in the 6 position, but also in the 5, 7 or 8 position, and is preferably CN or NO$_2$, also preferably CHO, ACO (especially acetyl), CF$_3$CO, AOOC (especially methoxycarbonyl or ethoxycarbonyl), ACOO (especially acetoxy), as well as preferably F, Cl, Br, I, CF$_3$, H$_2$NCO, H$_2$NCS or NH$_2$.

The radical $R^8$ is preferably H, as well as preferably methyl or ethyl.

$R^9$ is preferably vinyl, ethynyl, OH, OA (especially methoxy or ethoxy), COOH, COOA (especially methoxycarbonyl or ethoxycarbonyl), COOCH$_2$C$_6$H$_5$, NH$_2$, CN or phenyl.

Accordingly, $R^5$ is preferably phenyl, allyl, propargyl, 2-hydroxyethyl, 2-methoxyathyl, 2-ethoxyethyl, carboxymethyl, methoxycarbonylmethyl, ethoxycarbonylmethyl, benzyloxy-carbonylmethyl, 2-aminoethyl, cyanomethyl, 2-cyanoethyl or benzyl Accordingly, the invention especially relates to those compounds of the formula I in which at least one of the said radicals has one of the meanings indicated above as preferred Some preferred groups of compounds can be expressed by the formulae Ia to Ii hereinafter, which correspond to the formula I and in which the radicals which are not defined in detail have the meaning indicated for the formula I, but in which

| | | |
|---|---|---|
| in Ia | $R^1$ and $R^2$ | are each A; |
| in Ib | $R^1$ and $R^2$ | are each CH$_3$; |
| in Ic | $R^1$ and $R^2$ | together are alkylene with 3–6 C atoms; |
| in Id | $R^5$ | is phenyl, allyl, propargyl, 2-hydroxyethyl, 2-AO-ethyl, carboxymethyl, AO—CO—CH$_2$, benzyloxycarbonylmethyl, 2-aminoethyl, cyanomethyl, 2-cyanoethyl or benzyl; |
| in Ie | $R^5$ | is phenyl, allyl, propargyl, 2-hydroxyethyl, carboxymethyl, methoxy- |
| | | carbonylmethyl, benzyloxycarbonylmethyl, 2-aminoethyl, cyanomethyl or benzyl; |
| in If | $R^5$ | is allyl; |
| in Ig | $R^1$ and $R^2$ | are each CH$_3$ or together are —(CH$_2$)$_4$— or —(CH$_2$)$_5$—, |
| | $R^5$ | is phenyl, allyl, propargyl, 2-hydroxyethyl, 2-AO-ethyl, carboxymethyl, AO—CO—CH$_2$, benzyloxycarbonylmethyl, 2-aminoethyl, cyanomethyl, 2-cyanoethyl or benzyl and |
| | $R^8$ | is H or CH$_3$; |
| in Ih | $R^1$ and $R^2$ | are each CH$_3$, |
| | $R^5$ | is phenyl, allyl, propargyl, 2-hydroxyethyl, carboxymethyl, methoxycarbonylmethyl, benzyloxycarbonylmethyl, 2-aminoethyl, cyanomethyl or benzyl and |
| | $R^8$ | is H; |
| in Ii | $R^1$ and $R^2$ | are each CH$_3$, |
| | $R^5$ | is allyl and |
| | $R^8$ | is H. |

Additionally preferred are compounds of the formulae I' and Ia' to Ii' which correspond to the formulae I and Ia to Iii but in which in each case additionally $R^3$ is H, OH, OCHO or OCOCH$_3$ and $R^4$ is H, especially those compounds of the formulae I' and Ia' to Ii' in which in each case additionally $R^3$ is OH and $R^4$ is H.

Additionally preferred are compounds of the formulae I'' and Ia'' to Ii'' which correspond to the formulae I and Ia to Ii but in which in each case additionally $R^3$ and $R^4$ together are a bond.

Furthermore preferred are compounds of the formulae I, I', I'', Ia to Ii, Ia' to Ii' and Ia'' to Ii'' in which in each case additionally (a) $R^6$ is different from H and
  $R^7$ is H;
(b) $R^6$ is different from H and is located in the 6 position and
  $R^7$ is H;
(c) $R^6$ is NO$_2$, CN, CHO, ACO, HOOC, AOOC, ACOO, F, Cl, Br, I, CF$_3$, H$_2$NCO, H$_2$NCS or NH$_2$ and
  $R^7$ is H;
(d) $R^6$ is NO$_2$, CN, CHO, ACO, HOOC, AOOC, ACOO, F, Cl, Br, I, CF$_3$, H$_2$NCO, H$_2$NCS or NH$_2$, and is located in the 6 position and
  $R^7$ is H;
(e) $R^6$ is NO$_2$, CN, Br or CH$_3$OOC and
  $R^7$ is H;
(f) $R^6$ is NO$_2$, CN, Br or CH$_3$OOC, and is located in the 6 position and
  $R^7$ is H;
(g) $R^6$ is NO$_2$ or CN and
  $R^7$ is H;
(h) $R^6$ is NO$_2$ or CN, and is located in the 6 position and
  $R^7$ is H;
(i) $R^6$ is CN and
  $R^7$ is H;
(j) $R^6$ is CN, and is located in the 6 position and
  $R^7$ is H.

Otherwise, hereinbefore and hereinafter the radicals $R^1$ to $R^8$, A, "alkyl" and Ac have the meanings indicated for formula I, unless expressly indicated otherwise.

The invention furthermore relates to a process for the preparation of chroman derivatives of the formula I according to claim 1, characterized in that a chroman of the formula II

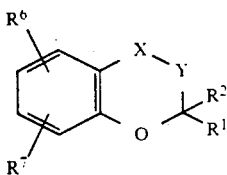

in which
X-Y is

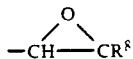

or —CHE-CR³R⁸— and
E is Cl, Br, I or a reactive esterified OH group, and R¹, R², R³, R⁶, R⁷ and R⁸ have the meanings indicated for formula I, is reacted with a compound of the formula III

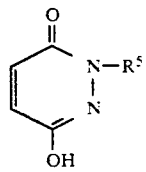  III in which R⁵ has the meaning indicated for formula I, or with one of the reactive derivatives thereof, or in that a compound of the formula IV

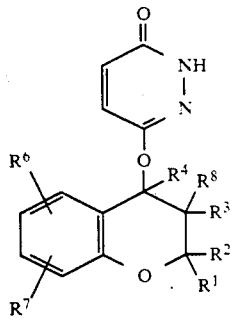  IV in which R¹, R², R³, R⁴, R⁶, R⁷ and R⁸ have the meanings indicated for formula I or one of the reactive derivatives thereof, is reacted with a compound of the formula

E-R⁵    V in which R⁵ and E have the meanings indicated for formula I and for formula II respectively, or one of the reactive derivatives thereof,
and/or in that a compound of the formula I in which R³ is OH and R⁴ is H is dehydrated and/or in that one or more of the radicals R³, R⁵, R⁶ and/or R⁷ in a compound of the formula I are converted into other radicals R³, R⁵, R⁶ and/or R⁷ and/or in that a basic compound of the formula I is converted into one of its acid addition salts by treatment with an acid.

The compounds of the formula I are otherwise prepared by methods known per se, as are described in the literature (for example in the standard works such as Houben-Weyl, Methoden der organischen Chemie [Methods of organic chemistry], Georg-Thieme-Verlag, Stuttgart; Organic Reactions, John Wiley & Sons, Inc., New York; and in the abovementioned patent applications), specifically under reaction conditions which are known and suitable for the said reactions. It is also possible in this connection to make use of variants which are known per se but not mentioned in detail here.

The starting materials can, if desired, also be formed in situ, in such a way that they are not isolated from the reaction mixture but are immediately reacted further to give the compounds of the formula I.

The compounds of the formula I are preferably prepared by reaction of compounds of the formula II with compounds of the formula III, preferably in the presence of an inert solvent at temperatures between about 0° and 150°.

Starting materials of the formula II with X-Y=

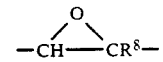

(3,4-epoxychromans) are preferred.

The starting materials II and III are known as a rule (compare, for example, German Offenlegungsschrift 3,726,261). Where they are unknown, they can be prepared by methods known per se. Thus, the starting materials of the formula II

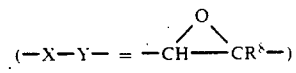

can be obtained by reaction of 2-hydroxyacetophenones of the formula 2-HO-R⁶R⁷C₆H₂-COCH₃ with ketones of the formula R¹-CO-R² to give corresponding 4-chromanones of the formula VIa

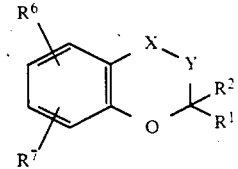

VIa —X—Y— = —CO—CH₂—

VIb —X—Y— = —CO—C(=CH—R¹¹)—

VIc —X—Y— = —CHOH—CHR⁸—

VId —X—Y— = —CH=CR⁸—

VIe —X—Y— = —CHBr—CR⁸OH— where appropriate condensation with aldehydes of the formula R¹¹-CHO (R¹¹=alkyl with 1–5 C atoms) to give 3-alkylidene-4-chromanones of the formula VIb, reduction for example with NaBH₄, to give chromanols of the formula VIc, dehydration, for example with p-toluenesulfonic acid, to give chromenes of the formula VId and oxidation, for example with 3-chloroperbenzoic acid. The latter oxidation can also be carried out in several stages. Thus, it is possible, for example with N-bromosuccinimide in aqueous solution, first to prepare the bromohydrins of the formula VIe, and subsequently to eliminate HBr from the latter with a base, for example sodium hydroxide solution.

The chromenes of the formula VId can also be obtained by condensation of salicylaldehydes of the formula 2-HO-$R^6R^7$-$C_6H_2$-CHO with ketones of the formula $R^1$-CO-$CH_2$-$R^8$ to give hydroxy ketones of the formula 2-HO-$R^6R^7C_6H_2CH=CR^8$-CO-$R^1$, reaction with organo-Li compounds of the formula $R^2$-Li, subsequent hydrolysis to give diols of the formula 2-HO-$R^6R^7C_6H_2$-CH=$CR^8$-$CR^1R^2$-OH and cyclisation with elimination of water.

Particularly suitable "reactive esterified OH groups" in compounds of the formulae II (-X-Y- = -CHE-$CR^3R^8$-) and V are the esters with alkylsulfonic acids (in which the alkyl group contains 1-6 C atoms) or with arylsulfonic acids (in which the aryl group contains 6-10 C atoms). These compounds can be obtained from the 4-chromanols of the formula VIc or from compounds of the formula $R^5$-OH by reaction with an inorganic acid halide such as $PCl_3$, $PBr_3$, $SOCl_2$ or $SOBr_2$, or with a sulfonyl chloride such as methane- or p-toluenesulfonyl chloride.

Suitable reactive derivatives of III are the appropriate salts, for example the Na or K salts, which can also be produced in situ.

It is preferable to carry out the reaction of II with III in the presence of a base. Examples of suitable bases are alkali metal or alkaline earth metal hydroxides, carbonates, alcoholates, hydrides or else amides such as NaOH, KOH, $Ca(OH)_2$, $Na_2CO_3$, $K_2CO_3$, Na or K methylate, ethylate or tert.-butylate, NaH, KH, $CaH_2$, $NaNH_2$, $KNH_2$, as well as organic bases such as triethylamine or pyridine, which can also be used in excess and then simultaneously act as solvent Particularly suitable inert solvents are alcohols such as methanol, ethanol, isopropanol, n-butanol or tert.-butanol; ethers such as diethyl ether, diisopropyl ether, tetrahydrofuran or dioxanes; glycol ethers such as ethylene glycol monomethyl or monoethyl ether (methylglycol or ethylglycol), ethylene glycol dimethyl ether (diglyme); ketones such as acetone or butanone; nitriles such as acetonitrile; nitro compounds such as nitromethane or nitrobenzene; esters such as ethyl acetate; amides such as dimethylformamide (DMF), dimethylacetamide or phosphoric hexamethyltriamide; sulfoxides such as dimethyl sulfoxide (DMSO); chlorinated hydrocarbons such as dichloromethane, chloroform, trichloroethylene, 1,2-dichloroethane or carbon tetrachloride; hydrocarbons such as benzene, toluene or xylene. Also suitable are mixtures of these solvents with one another The epoxide II

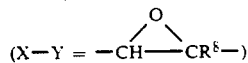

also be prepared in situ, for example by the act a base on the corresponding bromohydrin VIe.

A particularly preferred procedure comprises using an alcohol (for example ethanol) as solvent and adding an organic base (for example pyridine), with boiling preferably for about 0.5 to 20 hours Compounds of the formula I can also be prepared by reacting a compound of the formula IV with a compound of the formula V, preferably under the conditions of an N-arylation or N-alkylation in the presence or absence of one of the said inert solvents (for example acetone) at temperatures between about 0° and about 150°, it being advantageous for one of the said bases (for example potassium carbonate) to be present.

The preparation of the starting materials of the formula IV is described, for example, in EP-A 0,273,262; it is easily achieved, for example, by reaction of a compound of the formula II with 3-hydroxy-1,6-dihydro-6-pyridazinone (=3,6-pyridazinediol; formula III, but H in place of $R^5$). The starting materials of the formula V are known as a rule.

In place of the starting materials of the formula IV or V, it is also possible to use reactive derivatives thereof, for example in place of IV the corresponding K or Na salts, in place of 2-amino- or 2-hydroxy-1-E-alkenes of the formula V [$R^5$=-$CH_2$-CH($NH_2$)-$C_{n-2}H_{2n-4}$ or -$CH_2$-CHOH-$C_{n-2}H_{2n-4}$] the corresponding alkyleneimines (aziridine, 2-methylaziridine) or the corresponding alkylene oxides (ethylene oxide, propylene oxide); it may be preferable in the latter cases to employ elevated pressure (up to about 100 bar).

A compound of the formula I, in which $R^3$ is OH and $R^4$ is H can be converted by treatment with a dehydrating agent into a compound of the formula I in which $R^3$ and $R^4$ together are a bond. This is achieved, for example, by the action of one of the stated bases, for example NaH, in one of the stated solvents, for example DMSO, at temperatures between 0° and 150°.

The dehydration can also be carried out in several stages by converting, for example, the carbinol I ($R^3$=OH, $R^4$=H) into an ester, for example a sulfonic ester, such as a camphorsulfonic ester and treating the latter with a base, for example with NaOH.

It is furthermore possible to convert one or more of the radicals $R^3$, $R^5$, $R^6$ and/or $R^7$ in a compound of the formula I into other radicals $R^3$, $R^5$, $R^6$ and/or $R^7$.

For example, it is possible to replace an H atom by a halogen atom by halogenation, or by a nitro group by nitration, and/or to hydrolyse an ester group to a carbonyl group to a carboxyl group (for example on Pd-C in methanol) and/or to esterify a carboxyl group and/or to reduce a nitro group to an amino group and/or to alkylate or acylate an amino or hydroxyl group and/or to convert a cyano group (for example with HCl in water/methanol at 20°-100°) into a carboxyl group or (for example with Raney-nickel in water/acetic acid/pyridine in the presence of sodium phosphate) into a formyl group or (for example with KOH in tert.-butanol) into a carbamoyl group or (for example with $H_2S$ in pyridine/triethylamine) into a thiocarbamoyl group.

Nitration is achieved under customary conditions, for example with a mixture of concentrated $HNO_3$ and concentrated $H_2SO_4$ at temperatures between 0° and 30°.

Halogenation can be carried out, for example with elemental chlorine or bromine in one of the customary inert solvents at temperatures between about 0° and 30°.

A primary or secondary amino group and/or an OH group can be converted by treatment with alkylating agents into the corresponding secondary or tertiary amino group and/or alkoxy group. Examples of suitable alkylating agents are compounds of the formulae A-Cl, A-Br or A-I or corresponding sulfuric or sulfonic esters such as methyl chloride, bromide, iodide, dimethyl sulfate and methyl p-toluenesulfonate. It is furthermore possible, for example, to introduce one or two methyl groups with formaldehyde in the presence of formic acid. The alkylation is preferably carried out in the presence or absence of one of the said inert solvents, for example DMF, at temperatures between about 0° and about 120°, it also being possible for a catalyst to be present, preferably a base such as potassium tert.-butylate or NaH.

Suitable and preferred acylating agents for the acylation of amino or hydroxyl groups are the halides (for example chlorides or bromides) or anhydrides of carboxylic acids of the formula Ac-OH, for example acetic anhydride, propionyl chloride, isobutyryl bromide, formic acid/acetic anhydride and benzoyl- chloride It is possible to add a base such as pyridine or triethylamine in the acylation The acylation is preferably carried out in the presence or absence of an inert solvent, for example a hydrocarbon such as toluene, or a nitrile such as acetonitrile, or an amide such as DMF or an excess of a tertiary base such as pyridine or triethylamine at temperatures between about 0° and about 160°, preferably between 20° and 120°. Formylation is also achieved with formic acid in the presence of pyridine or with a mixture of formic acid and acetic anhydride.

A base of the formula I can be converted with an acid into the relevant acid addition salt. Particularly suitable acids for this reaction are those which provide physiologically acceptable salts Thus, it is possible to use inorganic acids, for example sulfuric acid, nitric acid, hydrohalic acids such as hydrochloric acid or hydrobromic acid, phosphoric acids such as orthophosphoric acid, sulfamic acid, as well as organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthaline-mono- and -disulfonic acids and lauryl sulfuric acid. Salts with physiologically unacceptable acids, for example picrates, can be used for purifying the compounds of the formula I.

The compounds of the formula I can have one or more chiral centres The preparation thereof may therefore result in racemates or, if optically active starting materials are used, an optically active form. If the compounds have two or more chiral centres, they may be produced in the synthesis as mixtures of racemates, from which the individual racemates can be isolated in pure form, for example by recrystallization from inert solvents. Thus, for example, compounds of the formula I in which $R^1 = R^2$, $R^3$ is OH and $R^4$ is H can have two chiral centres; however, the preparation by reaction of II with III results very predominantly in only one racemate with the OH group in the 3 position being trans to the 1-$R^5$-1,6-dihydro-6-oxo-pyridazinyl-3-oxy group in the 4 position. Racemates which are obtained can, if desired, be resolved into their enantiomers by mechanical, chemical or biochemical methods known per se. Thus, diastereomers can be formed from the racemate by reaction with an optically active resolving agent. Examples of suitable resolving agents for basic compounds of the formula I are optically active acids such as the D and L forms of tartaric acid, dibenzoyltartaric acid, diacetyltartaric acid, camphanic acid, camphorsulfonic acids, mandelic acid, malic acid or lactic acid. Carbinols (I, $R^3$=OH) can also be esterified using chiral acylating reagents, for example D- or L-α-methylbenzyl isocyanate, and then resolved (compare EP-A1 120,428). The various forms of the diastereomers can be separated in a manner known per se, for example by fractional crystallization, and the enantiomers of the formula I can be liberated from the diastereomers in a manner known per se. Separations of enantiomers are furthermore achieved by chromatography on optically active support materials.

The compounds of the formula I and the physiologically acceptable salts thereof can be used for the preparation of pharmaceutical formulations, in particular by non-chemical means. This can entail them being converted together with at least one solid, liquid and/or semi-liquid vehicle or auxiliary and, where appropriate, in combination with one or more other active compound(s) into a suitable dosage form.

The invention also relates to agents, in particular pharmaceutical formulations, containing at least one compound of the formula I and/or one of the physiologically acceptable salts thereof.

These formulations can be used as medicaments in human or veterinary medicine. Suitable vehicles are organic or inorganic substances which are suitable for enteral (for example oral), parenteral or topical administration and which do not react with the new compounds, for example water, vegetable oils, benzyl alcohols, polyethylene glycols, glycerol triacetate, gelatine, carbohydrates such as lactose or starch, magnesium stearate, talc, lanoline, vaseline Used for oral administration are, in particular, tablets, coated tablets, capsules, syrups, elixirs or drops, for rectal administration suppositories, for parenteral administration solutions, preferably oily or aqueous solutions, as well as suspensions, emulsions or implants, for topical administration ointments, creams, pastes, lotions, gels, sprays, foams, aerosols, solutions (for example solutions in alcohols such as ethanol or isopropanol, acetonitrile, DMF, dimethylacetamide, 1,2-propanediol or mixtures thereof and/or with water) or powders. The new compounds can also be freeze-dried, and the resulting lyophilisates used, for example, for the preparation of products for injection. Liposomal formulations are also suitable in particular for topical administration. The stated formulations can be sterilized and/or contain auxiliaries such as lubricants, preservatives, stabilizers and/or wetting agents, emulsifiers, salts to influence the osmotic pressure, buffer substances, colorants, flavourings and/or perfumes They can, if desired, also contain one or more other active compounds, for example one or more vitamins.

The compounds of the formula I and the physiologically acceptable salts thereof can be administered to humans or animals, in particular mammals such as monkeys, dogs, cats, rats or mice, and be used for the therapeutic treatment of the human or animal body and for the control of diseases, in particular for the therapy and/or prophylaxis of disorders of the cardiovascular system, in particular decompensated heart failure, angina pectoris, arrhythmia, peripheral or cerebral vascular disorders, and pathological states associated with high blood pressure, as well as diseases associated with changes in non-vascular muscles, for example asthma and urinary bladder incontinence.

This entails the substances according to the invention being administered, as a rule, in analogy to known antianginals or agents lowering blood pressure, for example nicorandil or cromakalim, preferably in dosages between about 0.01 and 5 mg, in particular between 0.02 and 0.5 mg, per dosage unit. The daily dosage is preferably between about 0.0001 and 0.1, in particular between 0.003 and 0.01 mg/kg of body weight. The specific dose for each particular patient depends, however, on a wide variety of factors, for example on the activity of the specific compound employed, on the age, body weight, the general state of health, sex, on the diet, on the time and route of administration, on the speed of elimination, medicament combination and severity of the particular disease for which the therapy is applied. Oral administration is preferred.

The compounds of the formula I and salts thereof are furthermore suitable for the treatment of alopecia areata, especially on topical administration. Used for this purpose, in particular, are pharmaceutical formulations which are suitable for topical treatment of the scalp and which are mentioned above. They contain about 0.005 to 10, preferably 0.5 to 5% by weight of at least one compound of the formula I and/or at least one of the salts thereof. Moreover, these compounds can be used for alopecia in analogy to the statements in WO 88/00822.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 18 041.7, filed Jun. 2, 1989, are hereby incorporated by reference.

Further "usual working up" means: if necessary, water is added, extraction is carried out with an organic solvent such as ethyl acetate, the organic phase is separated off, dried over sodium sulfate, filtered and evaporated, and purification is by chromatography and/or crystallization.

EXAMPLES

Example 1

A mixture of 1 g of 2,2-dimethyl-3,4-epoxy-6-cyano-chroman ("IIa"), 1.5 g of 3-hydroxy-1-phenyl-1,6-dihydropyridazin-6-one, 0.4 ml of pyridine and 35 ml of ethanol is boiled for 14 h. It is evaporated, the residue is chromatographed on silica gel, and 2,2-dimethyl-4-(1-phenyl-1,6-dihydro-6-oxo-pyridazinyl-3-oxy)-6-cyano-3-chromanol ("A"), is obtained, m.p. 203-206°.

The 2,2-dimethyl-4-(1-phenyl-1,6-dihydro-6-oxo-pyridazinyl-3-oxy)-3-chromanols below are obtained analogously from the corresponding epoxides:
6-Nitro-
6-Fluoro-
6-Chloro-
6-Bromo-
6-Trifluoromethyl-
6-Methoxycarbonyl-
6-Ethoxycarbonyl-.

Example 2

A mixture of 1 g of 2,2-dimethyl-4-(6-oxo-1,6-dihydropyridazinyl-3-oxy)-6-cyano-3-chromanol ("IVa"), 2 ml of allyl bromide, 3 g of potassium carbonate and 50 ml of acetone is boiled for 2 h; after this a further 2 ml of allyl bromide are added, and the mixture is boiled for a further 2 h. It is evaporated and worked up as usual, and 2,2-dimethyl-4-(1-allyl-1,6-dihydro-6-oxo-pyridazinyl-3-oxy)-6-cyano-3-chromanol is obtained, m.p. 145-146°.

The 2,2-dimethyl-6-cyano-3-chromanols below are obtained analogously:
4-(1-Propargyl-1,6-dihydro-6-oxo-pyridazin-yl-3-oxy)-, m.p. 185-186°
4-[1-(2-Methoxyethyl)-1,6-dihydro-6-oxo-pyridazinyl-3-oxy]-
4-[1-(2-Ethoxyethyl)-1,6-dihydro-6-oxo-pyridazinyl-3-oxy]-
4-[1-(2-Formylethyl)-1,6-dihydro-6-oxo-pyridazinyl-3-oxy]-
4-[1-(2-Acetylethyl)-1,6-dihydro-6-oxo-pyridazinyl-3-oxy]-
4-[1-(2-Thioacetylethyl)-1,6-dihydro-6-oxo-pyridazinyl-3-oxy]-
4-(1-Carboxymethyl-1,6-dihydro-6-oxo-pyridazinyl-3-oxy)-, m.p. 212-216°
4-(1-Methoxycarbonylmethyl-1,6-dihydro-6-oxo-pyridazinyl-3oxy)-, m.p. 170-172°
4-(1-Ethoxycarbonylmethyl-1,6-dihydro-6-oxo-pyridazinyl-3-oxy)-
4-(1-Benzyloxycarbonylmethyl-1,6-dihydro-6-oxo-pyridazinyl-3-oxy)-, m.p. 162-164°
4-[1-(2-Nitroethyl)-1,6-dihydro-6-oxo-pyridazinyl-3-oxy]-4-[1-(2-Dimethylaminoethyl)-1,6-dihydro-6-oxo-pyridazinyl-3-oxy]-
4-(1-Cyanomethyl-1,6-dihydro-6-oxo-pyridazinyl-3-oxy)-, m.p. 201-203°
4-[1-(2-Cyanoethyl)-1,6-dihydro-6-oxo-pyridazinyl-3-oxy]-4-[1-(2-Fluoroethyl)-1,6-dihydro-6-oxo-pyridazinyl-3-oxy]-
4-[1-(2,2,2-Trifluoroethyl)-1,6-dihydro-6-oxo-pyridazinyl-3-oxy]-
4-[1-(2-Methylthio-ethyl)-1,6-dihydro-6-oxo-pyridazinyl-3-oxy]-
4-[1-(2-Methylsulfinyl-ethyl)-1,6-dihydro-6-oxo-pyridazinyl-3-oxy]-
4-[1-(2-Methylsulfonyl-ethyl)-1,6-dihydro-6-oxo-pyridazinyl-3-oxy]-
4-(1-Benzyl-1,6-dihydro-6-oxo-pyridazinyl-3-oxy)-, m.p. 197-199°.

Also obtained analogously are the 2,2,3-trimethyl-6-cyano-3-chromanols below:
4-(1-Allyl-1,6-dihydro-6-oxo-pyridazinyl-3-oxy)-4-(1-Propargyl-1,6-dihydro-6-oxo-pyridazinyl-3-oxy)-4-[1-(2-Methoxyethyl)-1,6-dihydro-6-oxo-pyridazinyl-3-oxy]-
4-[1-(2-Ethoxyethyl)-1,6-dihydro-6-oxo-pyridazinyl-3-oxy]-
4-[1-(2-Formylethyl)-1,6-dihydro-6-oxo-pyridazinyl-3-oxy]-
4-[1-(2-Acetylethyl)-1,6-dihydro-6-oxo-pyridazinyl-3-oxy]-
4-[1-(2-Thioacetylethyl)-1,6-dihydro-6-oxo-pyridazinyl-3-oxy]-
4-(1-Carboxymethyl-1,6-dihydro-6-oxo-pyridazinyl-3-oxy)-4-(1-Methoxycarbonylmethyl-1,6-dihydro-6-oxo-pyridazinyl-3-oxy)-
4-(1-Ethoxycarbonylmethyl-1,6-dihydro-6-oxo-pyridazinyl-3-oxy)-
4-(1-Benzyloxycarbonylmethyl-1,6-dihydro-6-oxo-pyridazinyl-3-oxy)-

4-[1-(2-Nitroethyl)-1,6-dihydro-6-oxo-pyridazinyl-3-oxy]-4-[1-(2-Dimethylaminoethyl)-1,6-dihydro-6-oxo-pyridazinyl-3-oxy]-

4-(1-Cyanomethyl-1,6-dihydro-6-oxo-pyridazinyl-3-oxy)-4-[1-(2-Cyanoethyl)-1,6-dihydro-6-oxo-pyridazinyl-3-oxy]-4-[1-(2-Fluoroethyl)-1,6-dihydro-6-oxo-pyridazinyl-3-oxy]-4-[1-(2,2,2-Trifluoroethyl) 1,6-dihydro-6-oxo-pyridazinyl-3-oxy]-

4-[1-(2-Methylthio-ethyl)-1,6-dihydro-6-oxo-pyridazinyl-3-oxy]-

4-[1-(2-Methylsulfinyl-ethyl)-1,6-dihydro-6-oxo-pyridazinyl-3-oxy]-

4-[1-(2-Methylsulfonyl-ethyl)-1,6-dihydro-6-oxo-pyridazinyl-3-oxy]-

4-(1-Benzyl-1,6-dihydro-6-oxo-pyridazinyl-3-oxy)-;

the 2,2-dimethyl-6-nitro-3-chromanols below:

4-(1-Allyl-1,6-dihydro-6-oxo-pyridazinyl-3-oxy)- 4-(1-Propargyl-1,6-dihydro-6-oxo-pyridazinyl-3-oxy)-4-[1-(2-Methoxyethyl)-1,6-dihydro-6-oxo-pyridazinyl-3-oxy]-

4-[1-(2-Ethoxyethyl)-1,6-dihydro-6-oxo-pyridazinyl-3-oxy]-

4-[1-(2-Formylethyl)-1,6-dihydro-6-oxo-pyridazinyl-3-oxy]-

4-[1-(2-Acetylethyl)-1,6-dihydro-6-oxo-pyridazinyl-3-oxy]-

4-[1-(2-Thioacetylethyl)-1,6-dihydro-6-oxo-pyridazinyl-3-oxy]-

4-(1-Carboxymethyl-1,6-dihydro-6-oxo-pyridazinyl-3-oxy)-4-(1-Methoxycarbonylmethyl-1,6-dihydro-6-oxo-pyridazinyl-3-oxy)-

4-(1-Ethoxycarboxylmethyl-1,6-dihydro-6-oxo-pyridazinyl-3-oxy)-

4-(1-Benzyloxycarbonylmethyl-1,6-dihydro-6-oxo-pyridazinyl-3-oxy)-

4-[1-(2-Nitroethyl)-1,6-dihydro-6-oxo-pyridazinyl-3-oxy]-4-[1-(2-Dimethylaminoethyl)-1,6-dihydro-6-oxo-pyridazinyl-3-oxy]-

4-(1-Cyanomethyl-1,6-dihydro-6-oxo-pyridazinyl-3-oxy)-4-[1-(2-Cyanoethyl)-1,6-dihydro-6-oxo-pyridazinyl-3-oxy]-4-[1-(2-Fluoroethyl)-1,6-dihydro-6-oxo-pyridazinyl-3-oxy]-

4-[1 (2,2,2-Trifluoroethyl)-1,6-dihydro-6-oxo-pyridazinyl-3-oxy]-

4-[1-(2-Methylthio-ethyl)-1,6-dihydro-6-oxo-pyridazinyl-3-oxy]-

4-1-(2-Methylsulfinyl-ethyl)-1,6-dihydro-6-oxo-pyridazinyl-3-oxy]-

4-[1-(2-Methylsulfonyl-ethyl)-1,6-dihydro-6-oxo-pyridazinyl-3-oxy]-

4-(1-Benzyl-1,6-dihydro-6-oxo-pyridazinyl-3-oxy);

the 2,2-dimethyl-6-bromo-3-chromanols below:

4-(1-Allyl-1,6-dihydro-6-oxo-pyridazinyl-3-oxy)-4-(1-Propargyl-1,6-dihydro-6-oxo-pyridazinyl-3-oxy)- 4-[1-(2-Methoxyethyl)-1,6-dihydro-6-oxo-pyridazinyl-3-oxy]-

4-[1-(2-Ethoxyethyl)-1,6-dihydro-6-oxo-pyridazinyl-3-oxy]-

4-[1-(2-Formylethyl)-1,6-dihydro-6-oxo-pyridazinyl-3-oxy]-

4-[1-(2-Acetylethyl-)-1,6-dihydro-6-oxo-pyridazinyl-3-oxy]-

4-[1-(2-Thioacetylethyl)-1,6-dihydro-6-oxo-pyridazinyl-3-oxy]-

4-(1-Carboxymethyl-1,6-dihydro-6-oxo-pyridazinyl-3-oxy)-4-(1-Methoxycarbonylmethyl-1,6-dihydro-6-oxo-pyridazinyl-3-oxy)-

4-(1-Ethoxycarbonylmethyl-1,-6-dihydro-6-oxo-pyridazinyl-3-oxy)-

4-(1-Benzyloxycarbonylmethyl-1,6-dihydro-6-oxo-pyridazinyl-3-oxy)-

4-[1-(2-Nitroethyl)-1,6-dihydro-6-oxo-pyridazinyl-3-oxy]-4-[1-(2-Dimethylaminoethyl)-1,6-dihydro-6-oxo-pyridazinyl-3-oxy]-

4-(1-Cyanomethyl-1,6-dihydro-6-oxo-pyridazinyl-3-oxy)]-4-[1-(2-Cyanoethyl)-1,6-dihydro-6-oxo-pyridazinyl-3-oxy]-4-[1-(2-Fluoroethyl-)-1,6-dihydro-6-oxo-pyridazinyl-3-oxy]-4-[1-(2,2,2-Trifluoroethyl)-1,6-dihydro-6-oxo-pyridazinyl-3-oxy]-

4-[1-(2-Methyl-thio-ethyl)-1,6-dihydro-6-oxo-pyridazinyl-3-oxy]-

4-1(2-Methylsulfinyl-ethyl)-1,6-dihydro-6-oxo-pyridazinyl-3-oxy]-

4-[1-(2-Methylsulfonyl-ethyl)-1,6-dihydro-6-oxo-pyridazinyl-3-oxy]-

4-(1-Benzyl-1,6-dihydro-6-oxo-pyridazinyl-3-oxy)-;

the 2,2-dimethyl-6-methoxycarbonyl-3-chromanols below:

4-(1-Allyl-1,6-dihydro-6-oxo-pyridazinyl-3-oxy)-4-(1-Propargyl-1,6-dihydro-6-oxo-pyridazinyl-3-oxy)-4-[1-(2-Methoxyethyl)-1,6-dihydro-6-oxo-pyridazinyl-3-oxy]-

4-[1-(2-Ethoxyethyl)-1,6-dihydro-6-oxo-pyridazinyl-3-oxy]-

4-[1-(2-Formylethyl)-1,6-dihydro-6-oxo-pyridazinyl-3-oxy]-

4-[1-(2-Acetylethyl)-1,6-dihydro-6-oxo-pyridazinyl-3-oxy]-

4-[1-(2-Thioacetylethyl)-1,6-dihydro-6-oxo-pyridazinyl-3-oxy]-

4-(1-Carboxymethyl-1,6-dihydro-6-oxo-pyridazinyl-3-oxy)-4-(1-Methoxycarbonylmethyl-1,6-dihydro-6-oxo-pyridazinyl-3-oxy)-

4-(1-Ethoxycarbonylmethyl-1,6-dihydro-6-oxo-pyridazinyl-3-oxy)-

4-(1-Benzyloxycarbonylmethyl-1,6-dihydro-6-oxo-pyridazinyl-3-oxy)-

4-[1-(2-Nitroethyl)-1,6-dihydro-6-oxo-pyridazinyl-3-oxy]-4-[1-(2-Dimethylaminoethyl)-1,6-dihydro-6-oxo-pyridazinyl-3-oxy]-

4-(1-Cyanomethyl-1,6-dihydro-6-oxo-pyridazinyl-3-oxy)-4-[1-(2-Cyanoethyl)-1,6-dihydro-6-oxo-pyridazinyl-3-oxy]-4-[1-(2-Fluoroethyl)-1,6-dihydro-6-oxo-pyridazinyl-3-oxy]-

4-[1-(2,2,2-Trifluoroethyl)-1,6-dihydro-6-oxo-pyridazinyl-3-oxy]-

4-[1-(2-Methylthio-ethyl)-1,6-dihydro-6-oxo-pyridazinyl-3-oxy]-

4-[1-(2-Methylsulfinyl-ethyl)-1,6-dihydro-6-oxo-pyridazinyl-3-oxy]-

4-[1-(2-Methylsulfonyl-ethyl)-1,6-dihydro-6-oxo-pyridazinyl-3-oxy]-

4-(1-Benzyl-1,6-dihydro-6-oxo-pyridazinyl-3-oxy)-; and 2,2-Tetramethylene-4-(1-allyl-1,6-dihydro-6-oxo-pyridazinyl-3-oxy)-6-cyano-3-chromanol and 2,2-Pentamethylene-4-(1-allyl-1,6-dihydro-6-oxo-pyridazinyl-3-oxy)-6-cyano-3-chromanol.

Example 3

A mixture of 1 g of IVa, 0.67 ml of aziridine and 10 ml of dioxane is heated in a sealed tube at 130° for 3 h. It is evaporated, the residue is dissolved in dilute hydrochloric acid, and the solution is washed with dichloromethane, made alkaline and worked up as usual. The resulting 2,2-dimethyl-4-[1-(2-aminoethyl)-1,6-dihydro-6-oxo-pyridazinyl-3-oxy]-6-cyano-3-chromanol is recrystallized from acetonitrile/diethyl- ether 1:1. M.p. 1677°–169°.

The following 2,2-dimethyl-4-[1-(2-aminoethyl)-1,6-dihydro-6-oxo-pyridazinyl-3-oxy]-3-chromanols are obtained analogously:
6-Nitro-
6-Fluoro-
6-Chloro-
6-Bromo-
6-Trifluoromethyl-
6-Methoxycarbonyl-
6-Ethoxycarbonyl-.

Example 4

Ethylene oxide is passed into a mixture of 1 g of IVa, 1.6 g of $K_2CO_3$ and 35 ml of acetone while stirring and boiling for 8 h. The mixture is left to stand overnight and filtered, the filtrate is evaporated, and the usual working up results in 2,2-dimethyl-4-[1-(2-hydroxyethyl)-1,6-dihydro-6-oxo-pyridazinyl-3-oxy]-6-cyano-3-chromanol, m.p. 152–154 .

The following 2,2-dimethyl-4-[1-(2-hydroxyethyl)-1,6-dihydro-6-oxo-pyridazinyl-3-oxy]-3-chromanols are obtained analogously:
6-Nitro-
6-Fluoro-
6-Chloro-
6-Bromo-
6-Trifluoromethyl-
6-Methoxycarbonyl-
6-Ethoxycarbonyl-.

Example 5

1.2 g of 80% NaH are added to a solution of 2.82 g of 2,2-dimethyl-4-bromo-6-cyano-3-chromanol and 2.5 g of 3-hydroxy-1-phenyl-1,6-dihydro-6-pyridazinone in 70 ml of DMSO, and the mixture is stirred at 20° for 3 days. The usual working up results in "A", m.p. 203–206°.

Example 6

A mixture of 1 g of "A", 1.5 g of dl-camphor-10-sulphonyl chloride and 15 ml of pyridine is stirred at 90° for 1.5 h. It is evaporated, the residue is dissolved in ethyl acetate, the organic phase is washed with dilute hydrochloric acid and with water, dried over $Na_2SO_4$ and again evaporated, and the residue is dissolved in dichloromethane and purified by chromatography on silica gel. 1.1 g of a mixture of diastereomeric 4-camphorsulphonic esters are obtained and dissolved in 45 ml of methanol 6 g of NaOH on carrier (E. Merck, Cat. No. 1567) are added, the mixture is stirred at 20° for 16 h, evaporated and worked up as usual, and 2,2-dimethyl-4-(1-phenyl-1,6-dihydro-6-oxo-pyridazinyl-3-oxy)-6-cyano-3-chromene is obtained in addition to a little "A" (removed by chromatography).

Example 7

A solution of 1 g of 2,2-dimethyl-4-(1-benzyloxycarbonylmethyl-1,6-dihydro-6-oxo-pyridazinyl-3-oxy)-6-cyano-3-chromanol in 15 ml of methanol is hydrogenated on 0.3 g of 5% Pd-C at 20° and under 1 bar until cessation. The mixture is filtered and evaporated, and 2,2-dimethyl-4-(1-carboxymethyl-1,6-dihydro-6-oxo-pyridazinyl-3-oxy)-6-cyano-3-chromanol is obtained, m.p. 212–216°.

Example 8

A mixture of 2 g of "A", 11.7 ml of formic acid and 3.3 ml of acetic anhydride is left to stand at 20° for 16 h and then heated at 40–42° for 2 h. Evaporation and the usual working up result in 2,2-dimethyl-3-formyloxy-4-(1-phenyl-1,6-dihydro-6-oxo-pyridazinyl-3-oxy)-6-cyanochroman.

The following are obtained analogously from the corresponding 3-hydroxychromans:
2,2,3-Trimethyl-3-formyloxy-4-(1-phenyl-1,6-dihydro-6-oxo-pyridazinyl-3-oxy)-6-cyanochroman
2,2-Dimethyl-3-formyloxy-4-(1-allyl-1,6-dihydro-6-oxo-pyridazinyl-3-oxy)-6-cyanochroman
2,2,3-Trimethyl-3-formyloxy-4-(1-allyl-1,6-dihydro-6-oxo-pyridazinyl-3-oxy)-6-cyanochroman.

Example 9

A mixture of 1 g of "A" and 5 ml of acetic anhydride is boiled for 1 h. It is cooled and worked up as usual, and 2,2-dimethyl-3-acetoxy-4-(1-phenyl-1,6-dihydro-6-oxo-pyridazinyl-3-oxy)-6-cyanochroman is obtained.

The following are obtained analogously:
2,2,3-Trimethyl-3-acetoxy-4-(1-phenyl-1,6-dihydro-6-oxo-pyridazinyl-3-oxy)-6-cyanochroman
2,2-Dimethyl-3-acetoxy-4-(1-allyl-1,6-dihydro-6-oxo-pyridazinyl-3-oxy)-6-cyanochroman
2,2,3-Trimethyl-3-acetoxy-4-(1-allyl-1,6-dihydro-6-oxo-pyridazinyl-3-oxy)-6-cyanochroman.

Example 10

A solution of 1 g of 2,2-dimethyl-4-(1-phenyl-1,6-dihydro-6-oxo-pyridazinyl-3-oxy)-6-nitro-3-chromanol in 25 ml of methanol is hydrogenated on 0.5 g of 5% Pd-C at 20° and under 1 bar until cessation. The mixture is filtered and evaporated, and 2,2-dimethyl-4-(1-phenyl- 1,6-dihydro-6-oxo-pyridazinyl-3-oxy)-6-amino-3-chromanol is obtained.

The following is obtained analogously:
2,2,3-Trimethyl-4-(1-phenyl-1,6-dihydro-6-oxo-pyridazinyl-3-oxy)-6-amino-3-chromanol.

Example 11

A solution of 1 g of 2,2-dimethyl-4-(1-phenyl-1,6-dihydro-6-oxo-pyridazinyl-3-oxy)-6-amino-3-chromanol in 15 ml of HCOOH and 1 ml of pyridine is boiled for 19 h and evaporated. The usual working up results in 2,2-dimethyl-4-(1-phenyl-1,6-dihydro-6-oxo-pyridazinyl-3-oxy)-6-formamido-3-chromanol.

Example 12

A mixture of 1 g of 2,2-dimethyl-4-(1-phenyl-1,6-dihydro-6-oxo-pyridazinyl-3-oxy)-6-amino-3-chromanol, 10 ml of acetic anhydride and 10 ml of pyridine is left to stand at 20 for 16 h. It is evaporated and purified by chromatography, and 2,2-dimethyl-4-(1-phenyl-1,6-dihydro-6-oxo-pyridazinyl-3-oxy)-6-acetamido-3-chromanol is obtained.

Example 13

HCl is passed into a stirred boiling solution of 1 g of "A" in 50 ml of methanol and 2 ml of water for 14 h. It is left to cool and stand overnight. The precipitated 2,2-dimethyl-4-(1-phenyl-1,6-dihydro-6-oxo-pyridazinyl-3-oxy)-3-chromanol-6-carboxylic acid is filtered off.

Example 14

A mixture of 3 g of "A", 31 g of $Na_3PO_4 \cdot 12\ H_2O$, 28 ml of pyridine, 28 ml of water, 67 ml of acetic acid and 25 g of Raney Ni (moist with water) is stirred at 20° for 3 h. Filtration is followed by the usual working up, and 2,2-dimethyl-4-(1-phenyl-1,6-dihydro-6-oxo-pyridazinyl-3-oxy)-6-formyl-3-chromanol is obtained, m.p. 256–257°.

Example 15

3 g of "A" are dissolved in 40 ml of tert.-butanol and, while stirring, 5.6 g of powdered KOH are added. Boiling for 1 h and the usual working up result in 2,2-dimethyl-4-(1-phenyl-1,6-dihydro-6-oxo-pyridazinyl-3-oxy)-6-carbamoyl-3-chromanol.

Example 16

$H_2S$ is passed into a solution of 3 g of "A" in a mixture of 20 ml of pyridine and 10 ml of triethylamine at 20° for 5 h, the mixture is evaporated and worked up as usual, and 2,2-dimethyl-4-(1-phenyl-1,6-dihydro-6-oxo-pyridazinyl-3-oxy)-6-thiocarbamoyl-3-chromanol is obtained.

The examples which follow relate to pharmaceutical formulations which contain compounds of the formula I and/or physiologically acceptable salts thereof.

Example A

Tablets

A mixture of 1 g of 2,2-dimethyl-4-(1-allyl-1,6-dihydro-6-oxo-pyridazinyl-3-oxy)-6-cyano-3-chromanol, 4 kg of lactose, 1.2 kg of potato starch, 0.2 kg of talc and 0.1 kg of magnesium stearate is compressed to tablets in a customary manner, such that each tablet contains 0.1 mg of active compound.

Example B

Coated tablets

Tablets are compressed in analogy to Example A and are then coated in a customary manner with a coating composed of sucrose, potato starch, talc, tragacanth and colorant.

Example C

Capsules 1 kg of 2,2,3-trimethyl-4-(1-allyl-1,6-dihydro-6-oxo-pyridazinyl-3-oxy)-6-cyano-3-chromanol is packed in a customary manner into hard gelatin capsules so that each capsule contains 0.5 mg of active compound.

Example D

Ampoules

A solution of 10 g of Na salt of 2,2-dimethyl-4-(1-carboxymethyl-1,6-dihydro-6-oxo-pyridazinyl-3-oxy)-6-cyano-3-chromanol in 70 l of 1,2-propanediol is made up to 100 l with double-distilled water, filtered sterile, dispensed into ampoules and sealed sterile. Each ampoule contains 0.1 mg of active compound.

Tablets, coated tablets, capsules or ampoules which, contain one or more of the other active compounds of the formula I and/or physiologically acceptable salts thereof can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of chroman derivative of formula I

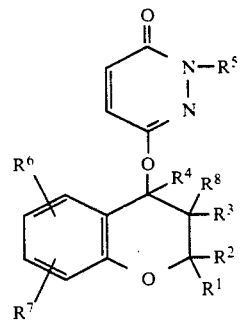

in which
$R^1$ is A,
$R^2$ and $R^8$ are each independently H or A, or
$R^1$ and $R^2$ together are $C_{3-6}$-alkylene.
$R^3$ is OH, OA or OAc,
$R^4$ is H, or
$R^3$ and $R^4$ together are a bond,
$R^5$ is Ar or $C_nH_{2n}\text{-}R^9$,
$R^9$ is $C_{2-4}$-alkenyl or $C_{2-4}$-alkynyl, OH, OA, CHO, CO-A, CS-A, COOH, COOA, COO-alkyl-Ar, CS-OA, $NO_2$, $NH_2$, NHA, $NA_2$, CN, F, Cl, Br, I, $CF_3$, SA, SO-A, $SO_2$-A or Ar.
Ar is a phenyl group which is unsubstituted or substituted once or twice by $R^{10}$,
$R^6$, $R^7$ and $R^{10}$ are each independently H, A, HO, AO, CHO, ACO, $CF_3CO$, ACS, HOOC, AOOC, AO-CS, ACOO, A-CS-O, hydroxy-alkyl, mercapto-alkyl, $NO_2$, $NH_2$, NHA, $NA_2$, CN, F, Cl, Br, I, $CF_3$, AS, ASO, $ASO_2$, AO-SO, $AO\text{-}SO_2$, AcNH, AO-CO-NH, $H_2NSO$, HANSO, $A_2NSO$, $H_2NSO_2$, $NANSO_2$, $A_2NSO_2$, $H_2NCO$, HANCO, $A_2NCO$, $H_2NCS$, HANCS, $A_2NCS$, ASONH, $ASO_2NH$, AOSONH, $AOSO_2NH$, ACO-alkyl, nitro-alkyl, cyanoalkyl, A-C(=NOH), A-C(=NNH_2), $H_2PO_3$ or $A_2PO_3$,
n is 1, 2 or 3,
A is $C_{1-6}$-alkyl,
-alkyl is $C_{1-6}$-alkylene, and
Ac is $C_{1-8}$-alkanoyl or $C_{7-11}$-aroyl,
or a salt thereof, comprising reacting a chroman of formula II

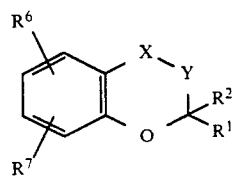

in which
X-Y is

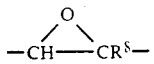

or —CHE-CR$^3$R$^8$— and

E is Cl, Br, I or a reactive esterified OH group, with a compound of the formula III

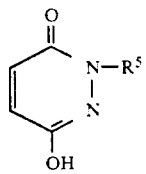

or with one of the reactive derivatives thereof and optionally further the compound of the formula I is converted into one of its acid addition salts by treatment with an acid.

2. A process according to claim 1, wherein:
A is unbranched $C_{1-6}$-alkyl, or $R^1$ and $R^2$ together are —$(CH_2)_x$— wherein x is 3–6;
Ac is $C_{1-6}$-alkanoyl;
$R^1$ and $R^2$ are each independently methyl or ethyl;
$R^3$ is OH;
$R^4$ is H;
Ar is unsubstituted phenyl;
n is 1 or 2; and
$R^6$ and $R^7$ are each independently methyl, ethyl, methoxy, ethoxy, acetyl, propionyl, thioacetyl, thiopropionyl, methoxycarbonyl, ethoxycarbonyl, methoxythiocarbonyl, ethoxythiocarbonyl, acetoxy, propionoxy, thio(no)acetoxy, thio(no)propionoxy, hydroxymethyl, 1- or 2-hydroxyethyl, mercaptomethyl, 1- or 2-mercaptoethyl, methylamino, ethylamino, dimethylamino, diethylamino, methylsulfinyl, ethylsulfinyl, methylsulfonyl, ethylsulfonyl, methoxy-sulfonyl, ethoxy-sulfonyl, acetamido, formamido, propionamido, benzamido, methoxycarbonylamino, ethoxycarbonylamino, methylaminosulfinyl, ethylaminosulfinyl, dimethylaminosulfinyl, diethylaminosulfinyl, methylaminosulfonyl, ethylaminosulfonyl, dimethylaminosulfonyl, diethylaminosulfonyl, N-methylcarbamoyl, N-ethylcarbamoyl, N,N-dimethylcarbamoyl, N,N-diethylcarbamoyl, N-methylthiocarbamoyl, N-ethyl-thiocarbamoyl, N,N-dimethyl-thiocarbamoyl, N,N-diethylthiocarbamoyl, methylsulfinylamino, ethylsulfinylamino, methylsulfonylamino, ethylsulfonylamino, methoxysulfinylamino, ethoxysulfinylamino, methoxysulfonylamino, ethoxysulfonylamino, 2-oxopropyl, 2-oxobutyl, 3-oxobutyl, 3-oxopentyl, nitromethyl, 1- or 2-nitroethyl, cyanomethyl, 1- or 2-cyanoethyl, 1-oximinoethyl, 1-oximinopropyl, 1-hydrazonoethyl or 1-hydrazonopropyl.

3. A process according to claim 1, wherein the compound of formula I is 2,2-dimethyl-4-(1-allyl-1,6-dihydro-6-oxo-pyridazinyl-3-oxy)-6-cyano-3-chromanol.

* * * * *

UNITED STATES PATENT AND TRADEMARK OFFICE
CERTIFICATE OF CORRECTION

PATENT NO. : 5,112,972

DATED : May 12, 1992

INVENTOR(S) : Rolf GERICKE et al.

It is certified that error appears in the above-identified patent and that said Letters Patent is hereby corrected as shown below:

On title page, item [75],

The fifth inventor's first name was not included:

Should read. . . .

JACQUES DE PEYER

Signed and Sealed this

Twenty-second Day of June, 1993

Attest:

MICHAEL K. KIRK

*Attesting Officer*     *Acting Commissioner of Patents and Trademarks*